(12) United States Patent
Purwar et al.

(10) Patent No.: US 11,007,381 B2
(45) Date of Patent: May 18, 2021

(54) INCREASED BEAM OUTPUT AND DYNAMIC FIELD SHAPING FOR RADIOTHERAPY SYSTEM

(71) Applicant: Varian Medical Systems, Inc., Palo Alto, CA (US)

(72) Inventors: Anuj Purwar, Pleasanton, CA (US); Dragos Constantin, Los Altos, CA (US); James Clayton, San Jose, CA (US)

(73) Assignee: Varian Medical Systems, Inc, Palo Alto, CA (US)

( * ) Notice: Subject to any disclaimer, the term of this patent is extended or adjusted under 35 U.S.C. 154(b) by 0 days.

(21) Appl. No.: 16/193,794

(22) Filed: Nov. 16, 2018

(65) Prior Publication Data

US 2019/0143144 A1 May 16, 2019

Related U.S. Application Data

(60) Provisional application No. 62/587,331, filed on Nov. 16, 2017.

(51) Int. Cl.
*A61N 5/10* (2006.01)
*H01J 35/14* (2006.01)
*H01J 35/08* (2006.01)

(52) U.S. Cl.
CPC ............. *A61N 5/1044* (2013.01); *A61N 5/10* (2013.01); *A61N 5/1042* (2013.01); *A61N 5/1043* (2013.01); *A61N 5/1045* (2013.01); *A61N 5/1047* (2013.01); *A61N 5/1077* (2013.01); *H01J 35/116* (2019.05); *H01J 35/14* (2013.01); *A61N 2005/1074* (2013.01); *A61N 2005/1089* (2013.01); *A61N 2005/1095* (2013.01)

(58) Field of Classification Search
CPC ...... A61N 5/10; A61N 5/1042; A61N 5/1043; A61N 5/1044; A61N 5/1045; A61N 5/1047; A61N 5/1077; A61N 2005/1074; H01J 35/116; H01J 35/14
USPC ........ 378/65, 98.6, 137, 138, 143, 145–147, 378/150–153
See application file for complete search history.

(56) References Cited

U.S. PATENT DOCUMENTS

| | | | | |
|---|---|---|---|---|
| 4,163,901 | A * | 8/1979 | Azam | H05H 9/00 315/5.42 |
| 4,914,681 | A | 4/1990 | Klingenbeck et al. | |
| 5,153,900 | A * | 10/1992 | Nomikos | A61N 5/1001 378/65 |
| 5,267,294 | A * | 11/1993 | Kuroda | A61N 5/1084 250/492.3 |
| 5,550,378 | A * | 8/1996 | Skillicorn | A61B 6/06 250/367 |

(Continued)

*Primary Examiner* — Allen C. Ho

(57) ABSTRACT

Systems and methods provide radiotherapy treatment by focusing an electron beam on an x-ray target (e.g., a tungsten plate) to produce a high-yield x-ray output with improved field shaping. A modified electron beam spatial distribution is employed to scan the x-ray target, such as a 2D periodic beam path, which advantageously lowers the x-ray target temperature compared to the typical compact beam spatial distribution. As a result, the x-ray target can produce a high yield output without sacrificing the x-ray target life span. The use of a 2D periodic beam path allows a much colder x-ray target functioning regime such that more dosage can be applied in a short period of time compared to existing techniques.

20 Claims, 11 Drawing Sheets

(56) References Cited

U.S. PATENT DOCUMENTS

| | | | | |
|---|---|---|---|---|
| 5,610,967 A * | 3/1997 | Moorman | A61B 6/06 | 378/141 |
| 5,625,663 A * | 4/1997 | Swerdloff | A61N 5/1042 | 378/113 |
| 5,682,412 A | 10/1997 | Skillicom et al. | | |
| 5,757,885 A * | 5/1998 | Yao | H05G 1/66 | 378/125 |
| 6,198,802 B1 * | 3/2001 | Elliott | A61B 6/032 | 378/101 |
| 6,234,671 B1 * | 5/2001 | Solomon | A61B 6/4441 | 250/492.3 |
| 6,445,766 B1 * | 9/2002 | Whitham | A61B 6/00 | 378/124 |
| 6,580,940 B2 * | 6/2003 | Gutman | A61N 5/1001 | 378/64 |
| 7,522,706 B2 * | 4/2009 | Lu | H05G 1/04 | 378/130 |
| 7,907,699 B2 * | 3/2011 | Long | A61N 5/1049 | 378/65 |
| 8,284,898 B2 * | 10/2012 | Ho | H05H 7/12 | 315/505 |
| 8,306,184 B2 * | 11/2012 | Chang | A61N 5/103 | 378/62 |
| 8,559,596 B2 * | 10/2013 | Thomson | A61N 5/1067 | 378/65 |
| 8,836,332 B2 * | 9/2014 | Shvartsman | A61B 5/055 | 324/318 |
| 8,903,471 B2 * | 12/2014 | Heid | A61N 5/1049 | 378/65 |
| 8,917,813 B2 * | 12/2014 | Maurer, Jr. | A61B 6/4014 | 378/65 |
| 8,958,864 B2 * | 2/2015 | Amies | A61N 5/1049 | 600/411 |
| 8,983,573 B2 * | 3/2015 | Carlone | A61N 5/1067 | 600/411 |
| 8,992,404 B2 * | 3/2015 | Graf | A61N 5/1045 | 600/1 |
| 9,079,027 B2 * | 7/2015 | Agano | G21K 1/02 | |
| 9,258,876 B1 * | 2/2016 | Cheung | H05H 7/02 | |
| 9,330,879 B2 * | 5/2016 | Lewellen | G21K 1/025 | |
| 9,468,777 B2 * | 10/2016 | Fallone | A61N 5/1049 | |
| 9,526,918 B2 * | 12/2016 | Kruip | A61N 5/1049 | |
| 9,583,302 B2 * | 2/2017 | Figueroa Saavedra | H01J 35/14 | |
| 9,786,054 B2 * | 10/2017 | Taguchi | A61N 5/1049 | |
| 9,786,465 B2 * | 10/2017 | Li | H01J 35/14 | |
| 9,801,594 B2 * | 10/2017 | Boyd | H01J 35/30 | |
| 9,844,358 B2 * | 12/2017 | Wiggers | A61B 6/587 | |
| 9,854,662 B2 * | 12/2017 | Mishin | H05H 9/02 | |
| 10,022,564 B2 * | 7/2018 | Thieme | A61B 6/4258 | |
| 10,080,912 B2 * | 9/2018 | Kwak | A61N 5/1048 | |
| 10,188,875 B2 * | 1/2019 | Kwak | A61N 5/1042 | |
| 10,212,800 B2 * | 2/2019 | Agustsson | A61N 5/1045 | |
| 10,272,264 B2 * | 4/2019 | Ollila | A61N 5/1039 | |
| 10,293,184 B2 * | 5/2019 | Pishdad | A61N 5/1049 | |
| 10,307,615 B2 * | 6/2019 | Ollila | A61N 5/1036 | |
| 10,449,389 B2 * | 10/2019 | Ollila | A61N 5/1047 | |
| 10,485,988 B2 * | 11/2019 | Kuusela | G21K 1/025 | |
| 10,636,609 B1 * | 4/2020 | Bertsche | A61B 6/4435 | |
| 10,660,588 B2 * | 5/2020 | Boyd | A61B 6/4021 | |
| 10,682,528 B2 * | 6/2020 | Ansorge | G01N 23/20 | |
| 10,758,746 B2 * | 9/2020 | Kwak | A61N 5/1065 | |
| 10,870,018 B2 * | 12/2020 | Bartkoski | G21K 1/093 | |
| 2010/0260317 A1 | 10/2010 | Chang et al. | | |
| 2014/0177807 A1 | 6/2014 | Lewellen et al. | | |
| 2014/0185776 A1 | 7/2014 | Li et al. | | |

* cited by examiner

US 11,007,381 B2

INCREASED BEAM OUTPUT AND DYNAMIC FIELD SHAPING FOR RADIOTHERAPY SYSTEM

CROSS-REFERENCE TO RELATED APPLICATIONS

This application claims the benefit of U.S. Provisional Patent Application No. 62/587,331 filed Nov. 16, 2017, entitled "INCREASED BEAM OUTPUT AND DYNAMIC FIELD SHAPING," by Anuj Purwar et al., which is hereby incorporated by reference.

FIELD

Embodiments of the present invention generally relate to the field of radiotherapy. More specifically, embodiments of the present invention relate to techniques for increasing and shaping the beam output of radiotherapy systems.

BACKGROUND

A basic goal of radiotherapy treatment is the irradiation of a target volume while minimizing the amount of radiation absorbed in healthy tissue. Shaping the electron beam is an important way of minimizing the absorbed dose in healthy tissue and critical structures. Conventional collimator jaws are used for shaping a rectangular treatment field; but, as usually treatment volume is not rectangular, additional shaping is required. On a linear accelerator, lead blocks or individually made Cerrobend blocks are attached onto the treatment head under standard collimating system. Another option is the use of multileaf collimator (MLC). Multileaf collimators are becoming the main tool for beam shaping of the x-rays on the linear accelerator. It is a simple and useful system in the preparation and performance of radiotherapy treatment.

Multileaf collimators are reliable, as their manufacturers developed various mechanisms for their precision, control and reliability, together with reduction of leakage and transmission of radiation between and through the leaves. Multileaf collimators are known today as a very useful clinical system for simple field shaping, but its use is getting even more important in dynamic radiotherapy, with the leaves moving during irradiation. This enables a precise dose delivery on any part of a treated volume. Volumetric modulated arc therapy (VMAT), the therapy of the future, is based on the dynamic use of MLC.

The problem with using MLC as a field shaping device is that they are relatively slow to alter shape and therefore relatively slow to alter the field shape, e.g., the treatment volume, to the patient. It would be advantageous to provide a system with a faster field shaping response time that might reduce the overall treatment time to the patient.

Moreover, radiation treatment systems employing MLC devices typically use focused electron beams that are directed to a tungsten target to generate the x-rays. Focused electron beams create a large amount of heat on the target that must be dissipated and managed. This typically means that the incident electron beam power/dosage rate must be reduced so that the life of the target can be extended. It would be advantageous to provide a radiation treatment system that could supply a higher dose rate while still maintaining extended life of the tungsten target.

SUMMARY OF THE INVENTION

Embodiments of the present invention describe systems and methods for providing radiotherapy treatment by focusing an electron beam on a target (e.g., a tungsten plate) to produce a high-yield x-ray output with improved field shaping. A modified electron beam spatial distribution is employed to scan the target, for example, in a two-dimensional (2D) periodic path, which advantageously lowers the x-ray target temperature compared to the typical compact beam spatial distribution. As a result, the x-ray target can produce a high yield output without sacrificing the x-ray target life span. The use of a 2D periodic beam path allows a much colder target functioning regime such that more dosage can be applied in a short period of time compared to existing techniques.

In addition to reducing heat concerns on the target, the annual beam distribution on the target creates x-ray fields can be used to provide custom dose applications to a patient where the dose applications can change shape and dose distribution much faster than would otherwise be provided or possible by use of a multileaf collimator. Therefore, embodiments of the present invention provide radiotherapy in faster durations, e.g., reduced treatment times. It is appreciated, that multileaf collimators (and blocks) can be used in conjunction with the x-ray fields generated via the annual beam distribution of the present invention to further shape the dose application to the patient.

According to one embodiment, a radiotherapy treatment system is disclosed including a computer system, an electron emission device for producing and emitting an electron beam, a target, a plurality of steering coils for providing magnetic fields in perpendicular directions for steering the electron beam to the target, where the target generates x-rays responsive to interaction with the electron beam, and a beam shaping device configured to be placed between the target and a patient, the beam shaping device operable to shape a treatment volume of the x-rays. The computer system includes instructions, that when executed, cause the computer system to control the plurality of steering coils to scan the electron beam across the target in a 2D periodic path to shape the distribution of x-rays.

According to one embodiment, the electron emission device includes an electron gun and a linear accelerator coupled to receive electrons from the electron gun and operable to produce the electron beam emitted from the electron emission device.

According to one embodiment, a shape of the 2D periodic path in combination with a physical configuration and orientation of the beam shaping device define a resultant treatment volume of x-rays exposed to the patient.

According to another embodiment, a radiotherapy treatment system is disclosed. The radiotherapy treatment system includes an electron emission device for producing and emitting an electron beam, a target, a plurality of steering coils for providing magnetic fields in perpendicular directions for steering the electron beam to the target where the target generates x-rays responsive to interaction with the electron beam, a control device coupled to the plurality of steering coils, and a beam shaping device including a multileaf collimator. The beam shaping device is configured to be placed between the target and a patient, and the beam shaping device operable to shape a treatment volume of the x-rays. The control device is operable to control the magnetic fields the plurality of steering coils to cause the electron beam to scan across the target in a 2D periodic path to produce x-rays and where further a shape of the 2D periodic path in combination with a physical configuration and orientation of the beam shaping device define a resultant treatment volume of the x-rays exposed to the patient.

According to one embodiment, the electron emission device includes an electron gun, and a linear accelerator coupled to receive electrons from the electron gun, and operable to produce the electron beam, where the electron beam is of approximately 200 to 300 MeV.

According to one embodiment, the 2D periodic path includes a Lissajous type path.

According to one embodiment, the 2D periodic path includes spherical harmonic based shapes.

According to one embodiment, the spherical harmonic based shapes include a linear combination of an s-wave shape, a p-wave shape, and a d-wave shape.

According to a different embodiment, a method of generating an x-ray treatment volume using a radiotherapy treatment system is disclosed. The method includes generating and emitting an electron beam using an electron emission device, steering the electron beam onto a target and dynamically scanning the electron beam across the target in a 2D periodic path, producing, via the target, and responsive to interaction with the electron beam being scanned thereon in accordance with the 2D periodic path, a 2D periodic distribution of x-rays, and producing a resultant treatment volume of the x-rays by shaping the 2D periodic distribution of x-rays using a beam shaping device, where a shape of the 2D periodic path in combination with a physical configuration and orientation of the beam shaping device define the resultant treatment volume of x-rays.

According to some embodiments, the method further includes adjusting at least one of a voltage and a current over a plurality of steering coils to scan said electron beam across said target in said 2D periodic path.

According to some embodiments, the 2D periodic path comprises a convex hull.

BRIEF DESCRIPTION OF THE DRAWINGS

The accompanying drawings, which are incorporated in and form a part of this specification and in which like numerals depict like elements, illustrate embodiments of the present disclosure and, together with the description, serve to explain the principles of the disclosure.

DETAILED DESCRIPTION

Figure 1:
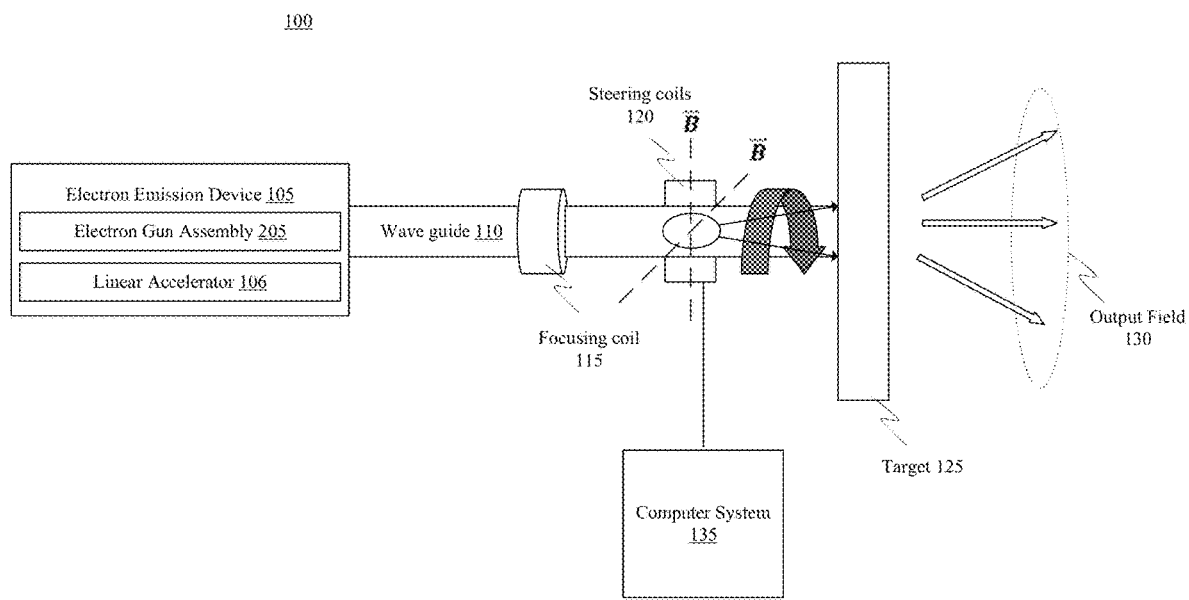
FIG. 1 depicts an exemplary radiotherapy system for scanning a 2D periodic electron beam path on a target to produce an x-ray field according to embodiments of the present invention.

Reference will now be made in detail to several embodiments. While the subject matter will be described in conjunction with the alternative embodiments, it will be understood that they are not intended to limit the claimed subject matter to these embodiments. On the contrary, the claimed subject matter is intended to cover alternative, modifications, and equivalents, which may be included within the spirit and scope of the claimed subject matter as defined by the appended claims.

Furthermore, in the following detailed description, numerous specific details are set forth in order to provide a thorough understanding of the claimed subject matter. However, it will be recognized by one skilled in the art that embodiments may be practiced without these specific details or with equivalents thereof. In other instances, well-known methods, procedures, components, and circuits have not been described in detail as not to unnecessarily obscure aspects and features of the subject matter.

Portions of the detailed description that follow are presented and discussed in terms of a method. Although steps and sequencing thereof are disclosed in a figure herein (e.g., FIGS. 9 and 10) describing the operations of this method, such steps and sequencing are exemplary. Embodiments are well suited to performing various other steps or variations of the steps recited in the flowchart of the figure herein, and in a sequence other than that depicted and described herein.

Some portions of the detailed description are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer-executed step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout, discussions utilizing terms such as "accessing," "displaying," "writing," "including," "storing," "rendering," "transmitting," "instructing," "associating," "identifying," "capturing," "controlling," "encoding," "decoding," "monitoring," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Increased Beam Output and Dynamic Field Shaping Using a 2D Periodic Electron Beam Path Embodiments of the present invention describe systems and methods for providing radiotherapy treatment using an electron emission device that produces an electron beam focused on a target (e.g., a tungsten plate) to generate a high-yield x-ray output with improved field shaping. The high-yield x-ray output and improved field shaping minimizes the radiation received by healthy tissue, increases the dosage rate/throughput of the treatment, and increases the useful lifetime of the tungsten target.

Embodiments according to the present invention use a modified electron beam spatial distribution, such as a 2D periodic beam distribution, to lower the x-ray target temperature compared to typical compact beam spatial distribution. The temperature of the target is reduced due to the 2D periodic path of the electron beam versus a compact beam profile, e.g., the heat generated from the electron beam is spread out within the target in accordance with the beam path. As a result, the electron beam output can be increased without sacrificing x-ray target life span. The use of a 2D periodic electron beam distribution allows a much colder target functioning regime such that more dosage can be applied in a short period of time compared to existing techniques. Further, the useful life of the tungsten target is increased.

According some embodiments of the present invention, the electron beam is scanned in one or more 2D periodic paths defined by one or more predetermined elementary shapes, such as Lissajous paths or spherical harmonic based shapes (e.g., s-wave, p-wave, d-wave, and so on), in order to increase the output and shape the electron beam profile. The 2D periodic path can be rapidly dynamically altered. The elementary shapes can constitute a new basis set, as compared to the Cartesian-style basis set used for multileaf collimators (MLCs). By dynamically shaping the electron field at the target it is possible to generate beam fluence appropriate for a tumor much faster than what an MLC can do. The MLC can still be used for leakage blocking at the edge of a field instead of primary beam shaping.

In some embodiments, the electron beam configuration is changed using external magnetic fields generated by specially designed coils. In other embodiments, hollow cathodes that generate 2D periodic beams are used, and the linear accelerator is designed such that the 2D periodic distribution is preserved along the accelerator. In yet other embodiments, existing steering coils are used to perform a scanning circular motion of the beam with a frequency higher than 200 kHz to ensure that one pulse gets smeared on the target surface in one revolution.

With regard to FIG. 1, an exemplary radiotherapy system 100 for generating a 2D periodic electron beam to the target is depicted according to embodiments of the present invention. An electron emission device 105 (e.g., an electron gun assembly 205) generates an electron beam and a waveguide 110 transports the electron beam to a focusing coil 115 to focus the electron beam using a magnetic field. According to some embodiments, the electron emission device 105 generates an electron beam at approximately 30 kV, for example. The electron beam may be accelerated by a linear accelerator 106 to approximately 200-300 MeV in accordance with well-known techniques and equipment.

A 2D periodic distribution of x-rays is achieved, in one embodiment, using a pair of magnetic steering coils 120 to deflect the electron beam in accordance with a predetermined path on the x-ray target surface 125. The x-ray target surface 125 may be a high-yield target surface in the form of a tungsten plate or wedge, for example. As described in more detail below, the pair of magnetic steering coils 120 can be dynamically controlled to deflect the electron beam along a 2D periodic path on the x-ray target surface 125. The use of a 2D periodic electron beam distribution allows a much colder target functioning regime by dynamically moving the electron beam over a wider surface area versus a concentrated electron beam distribution. Because of this, the target output field 130 can be increased substantially without sacrificing the life span of x-ray target surface 125. Dynamic electron beam scanning may be used to achieve a 2D periodic electron beam spatial distribution, and can also be used for dynamic field shaping by changing the scanning path using generalized curves.

The pair of magnetic steering coils 120 may include one or more pairs of magnetic steering coils that dynamically produce magnetic fields in perpendicular directions for steering the electron beam on the x-ray target surface 125. The magnetic field produced by pair of magnetic steering coils 120 may be controlled by computer system 135 (e.g., computer system 1100 depicted in FIG. 11), for example, by adjusting a voltage and/or current across the pair of magnetic steering coils 120. The 2D periodic electron beam distribution may be generated by varying a voltages or currents applied to the pair of magnetic steering coils 120, in combination, to produce predetermined elementary shapes, e.g., Lissajous paths or spherical harmonic based shapes (e.g., s-wave, p-wave, d-wave, and so on), or a linear combination thereof, in order to increase the output and shape the electron beam profile. The scanned 2D periodic electron beam path on x-ray target surface 125 causes to be generated an x-ray output field or distribution 130. Advantageously, this distribution 130 can be dynamically altered by corresponding dynamic adjustments of the pair of magnetic steering coils 120.

According to some alternative embodiments, the x-ray target surface 125 is not used and the radiotherapy system 100 is used to perform electron therapy.

Figure 2:
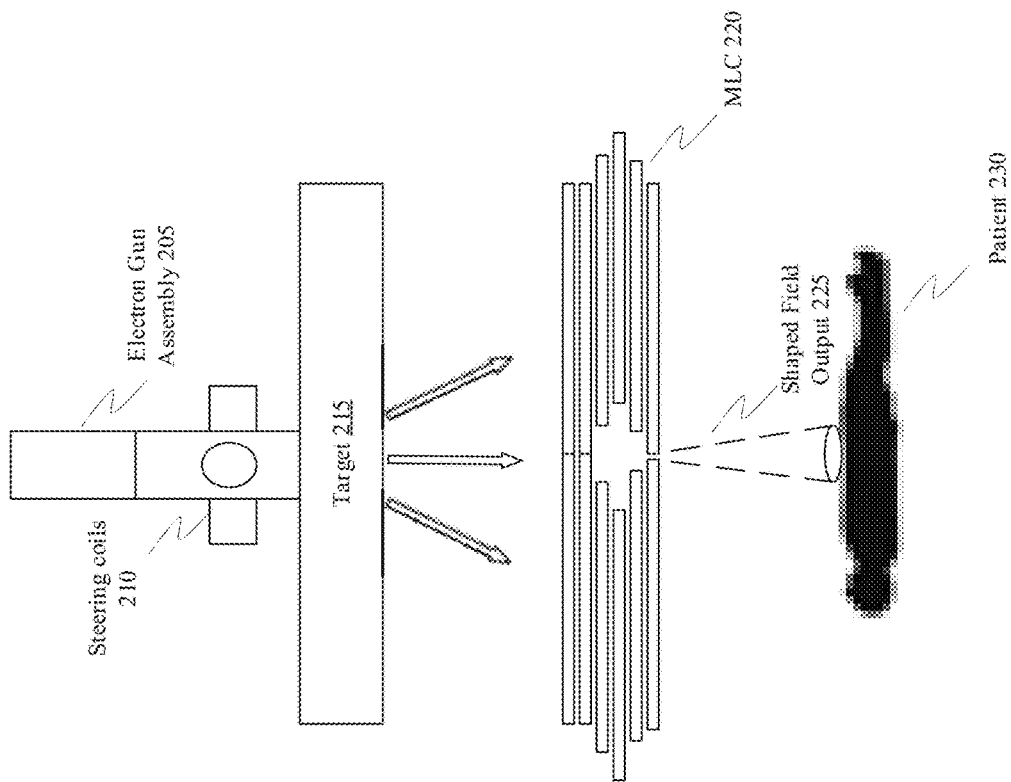
FIG. 2 depicts an exemplary radiotherapy system for generating a 2D periodic electron beam path on a target to produce x-rays shaped using a beam shaping device according to embodiments of the present invention.

In the example of FIG. 2, an exemplary radiotherapy system 200 for generating a 2D periodic electron beam to produce x-rays shaped using a beam shaping device (e.g., MLC 220) is depicted according to embodiments of the present invention. An electron gun assembly 205 generates an electron beam and a 2D periodic distribution of x-rays is achieved using a pair of magnetic steering coils 210 that generate opposed B-fields to deflect the electron beam on a 2D periodic path on the x-ray target surface 215. The use of a 2D periodic electron beam distribution allows a much colder target functioning regime such that more dosage can be applied in a short period of time compared to existing techniques. The MLC 220 may be used to further shape the x-ray distribution output from the x-ray target surface 215. In this fashion, the MLC 220 may be used for leakage blocking at the edge of the output field (instead of primary beam shaping). In this embodiment, the shaped field output 225 is shaped by the combination of the pair of magnetic steering coils 210 and the MLC 220, and is delivered to the target region of patient 230, for example, according to a treatment plan. In this embodiment, the dose application to the patient 230 can be altered by dynamically altering the signals to the pair of magnetic steering coils 210 as well as reconfiguration of the MLC 220. In effect, the MLC 220 can provide course shaping and the pair of magnetic steering coils 210 can provide fine shaping, etc., or vice-versa.

Figure 3:
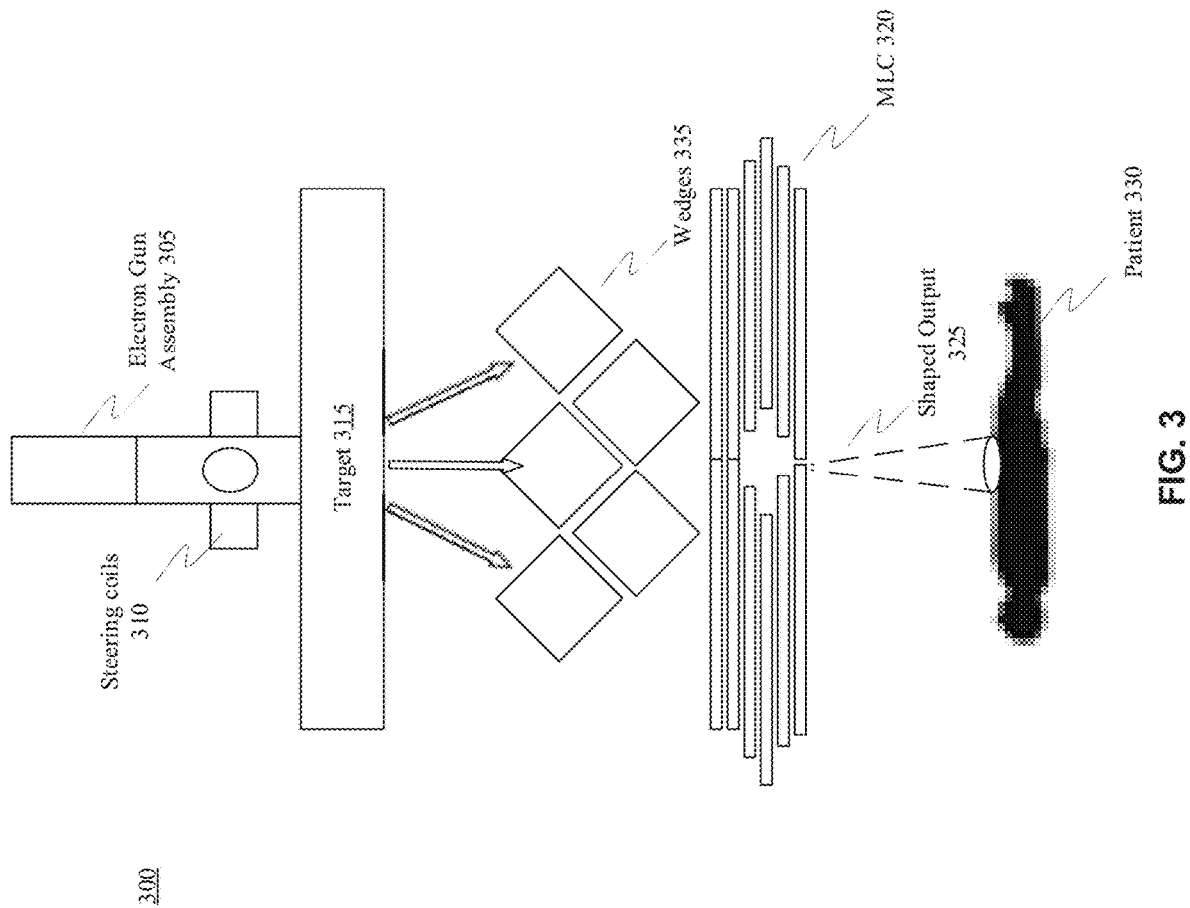
FIG. 3 depicts an exemplary radiotherapy system for generating a 2D periodic electron beam path to produce an x-ray field that is further shaped using an MLC in combination with blocks or wedges according to embodiments of the present invention.

In the embodiment of FIG. 3, an exemplary radiotherapy system 300 for generating a shaped x-ray distribution using: 1) a 2D periodic electron beam path on the x-ray target surface 315; and 2) an MLC 320 in combination with blocks or wedges 335 (e.g., lead blocks or Cerrobend blocks) is depicted according to embodiments of the present invention. An electron gun assembly 305 generates an electron beam and a 2D periodic distribution of x-rays is achieved using a pair of magnetic steering coils 310 to move the electron beam on a circular path on the x-ray target surface 315. The wedges 335 may be used to perform field shaping in addition to the MLC 320. The resultant shaped beam output 325 shaped by the pair of magnetic steering coils 310, the wedges 335, and the MLC 320 is delivered to the target region of patient 330, for example, according to a treatment plan.

Figure 4:
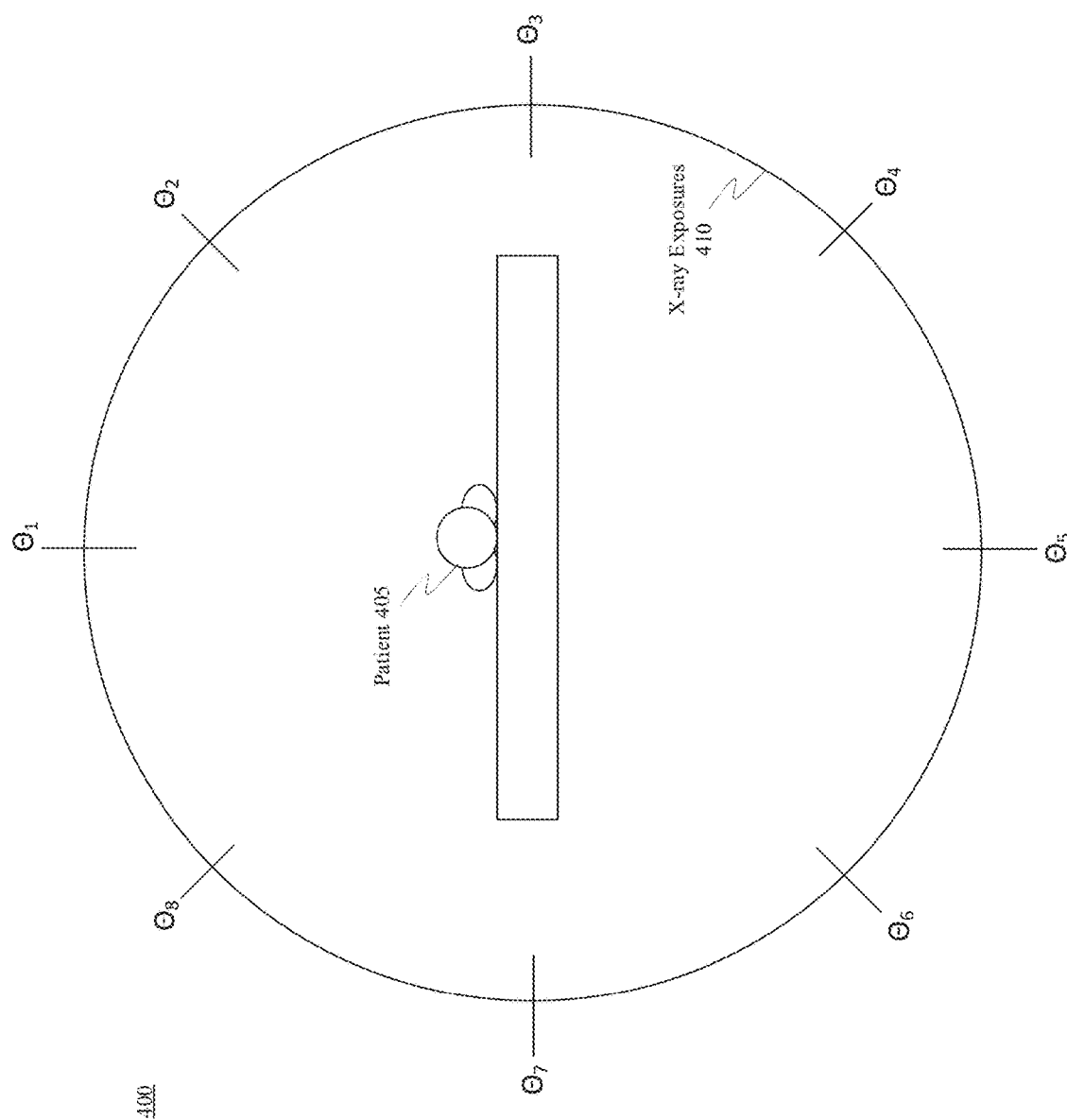
FIG. 4 depicts an exemplary tomographic patient imaging session for generating a patient treatment plan to perform radiotherapy using a 2D periodic distribution of x-rays according to embodiments of the present invention.

With regard to FIG. 4, an exemplary patient imaging session 400 for generating a patient treatment plan (e.g., a radiotherapy treatment plan) using a 2D periodic beam path is depicted according to embodiments of the present invention. The patient 405 is positioned at a center and radiation is emitted over a computerized tomography (CT) scan configured to combine a series of x-ray exposures 410 performed over different angles (e.g., $\Theta_1$-$\Theta_8$) around the patient 405. A computer system 135 controls the radiotherapy system (e.g., of FIG. 1-3) to radiate the patient at the different positions.

Figure 5:
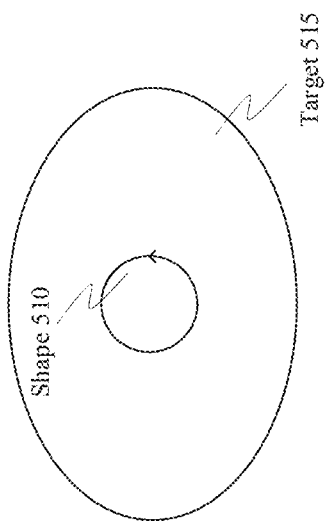
FIG. 5 depicts an exemplary circular (2D periodic) beam path generated using a pair of steering coils according to embodiments of the present invention.

FIG. 5 depicts an exemplary 2D periodic electron beam path 510 generated using a pair of magnetic steering coils as described herein according to embodiments of the present invention. The electron beam path 510 is scanned on a target 515 that generates an x-ray field for providing radiotherapy treatment. In this example, the 2D periodic beam path is roughly circular or annular.

Figure 6:
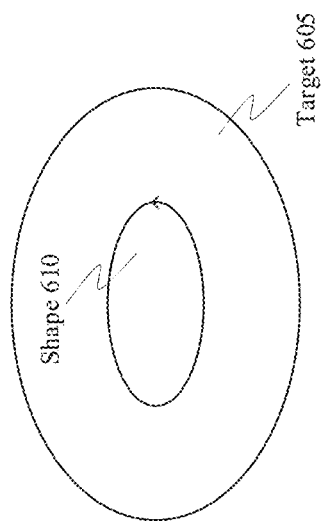
FIG. 6 depicts an exemplary elliptical (2D periodic) beam path generated using a pair of steering coils according to embodiments of the present invention.

FIG. 6 depicts an exemplary elliptical electron beam path 610 generated using a pair of magnetic steering coils as described herein according to embodiments of the present invention. The electron beam path 610 is scanned on a target 605 that generates an x-ray field for providing radiotherapy treatment.

Figure 7:
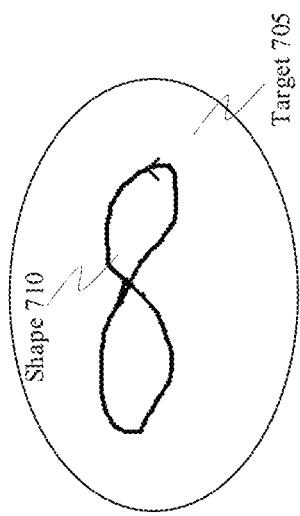
FIG. 7 depicts an exemplary figure-eight (2D periodic) beam path generated using a pair of steering coils according to embodiments of the present invention.

FIG. 7 depicts an exemplary figure-eight electron beam path 710 generated using a pair of magnetic steering coils as described herein according to embodiments of the present invention. The electron beam path 710 is scanned on a target 705 that generates an x-ray field for providing radiotherapy treatment.

According to some embodiments, electronic signals or commands are used to control a radiotherapy device for producing a corresponding beam path based on a patient's treatment plan and one or more predetermined elementary shapes (e.g., a circle, an ellipse, a figure-eight, a clover leaf, etc.). For example, multiple shapes may be selected, and each shape may be assigned a specific weight that indicates the desired beam intensity for the corresponding shape. In one example, an electronic (e.g., digital) signal or command is sent from a power management or control unit to a pair of steering coils to vary the current or voltage over the steering coils to produce a desired shape. Moving the electron beam with respect to the patient in this way reduces target heating and increase output of the radiotherapy system. During operation, a control signal, such as an arbitrary sine wave, may be used to trigger the radiotherapy system to generate an electron beam periodically.

According to some embodiments, the electronic signals or commands are used to control a radiotherapy device for producing arbitrary 2D shapes (e.g., a convex hull) using linear combinations of basic shape functions (e.g., a circle, an ellipse, a figure-eight, a clover leaf, etc.). Moreover, tiling two-dimensional projections of a treatment volume may be optimized for Rapid Arc type treatments that rapidly deliver precise intensity modulated radiation therapy (IMRT).

Figure 8:
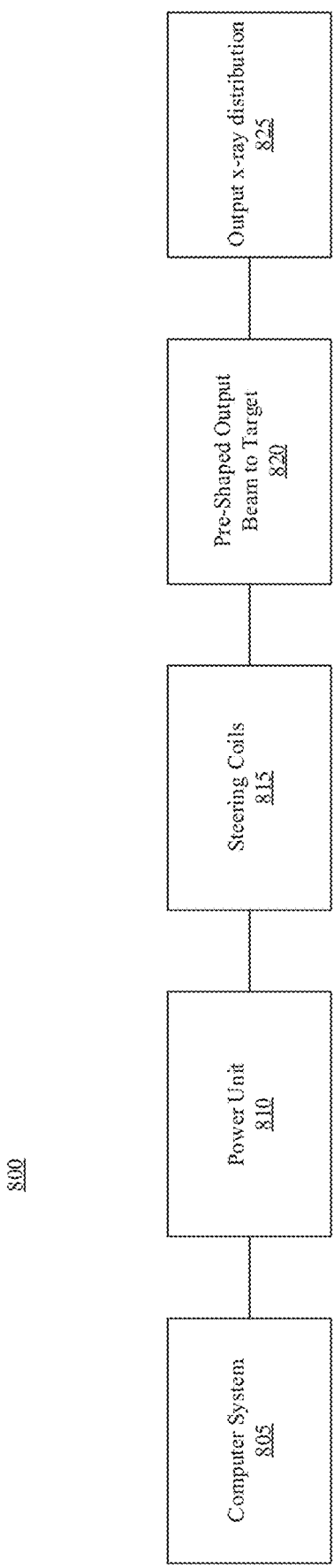
FIG. 8 depicts a block diagram and dataflow diagram of an exemplary radiotherapy treatment system for using a 2D periodic electron beam path to generate a 2D periodic field or distribution of x-rays to produce a treatment volume according to embodiments of the present invention.

As depicted in FIG. 8, according to some embodiments, a computer system 805 generates or accesses a patient treatment plan for providing radiotherapy using a radiotherapy treatment system 800. The patient treatment plan may include one or more pre-defined shapes associated with a treatment weight or magnitude. Based on the treatment plan (e.g., the shapes and weights), the computer system 805 sends one or more instructions to a power unit 810 of the radiotherapy treatment system for controlling steering coils 815 of the radio therapy treatment system 800 to generate electron beam paths according to the patient treatment plan. The power unit 810 may cause the steering coils 815 to shape the electron beam to produce the beam paths by varying a voltage or current of the control signals sent to the steering coils 810 as supplied by the power unit 810. The pre-shaped output beam is applied to a target 820 (e.g., a tungsten plate or wedge) that produces high-yield x-rays, and the resultant output x-ray distribution 825 is applied to a patient for performing radiotherapy on a target region thereof.

Figure 9:
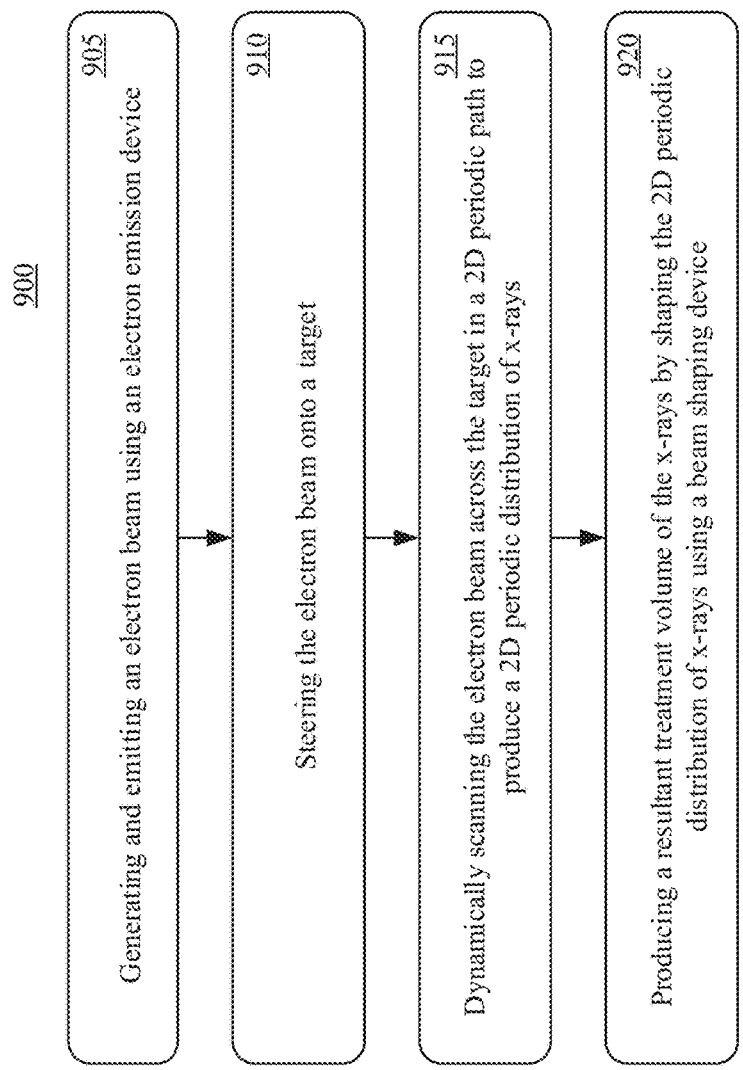
FIG. 9 is a flow chart depicting an exemplary sequence of computer implemented steps for automatically producing a 2D periodic distribution of x-rays using a 2D periodic electron beam path in a radiotherapy system according to embodiments of the present invention.

With regard to FIG. 9, an exemplary sequence of computer implemented steps 900 for automatically generating a 2D periodic beam distribution to produce a treatment volume of x-rays using a radiotherapy system is depicted according to embodiments of the present invention. At step 905, an electron beam is generated an emitted from an electron emission device, and the electron beam is steered onto a predetermined target at step 910, for example, according to a treatment plan. At step 915, the electron beam is dynamically scanned across the target in a 2D periodic path to produce a 2D periodic distribution of x-rays. At step 920, a resultant treatment volume of the x-rays is produced by shaping the 2D periodic distribution of x-rays using a beam shaping device. The resultant treatment volume generated at step 920 can provide higher dosages in a short period of time compared to existing techniques, and can extend the lifetime of the x-ray target by distributing heat across the target surface.

Figure 10:
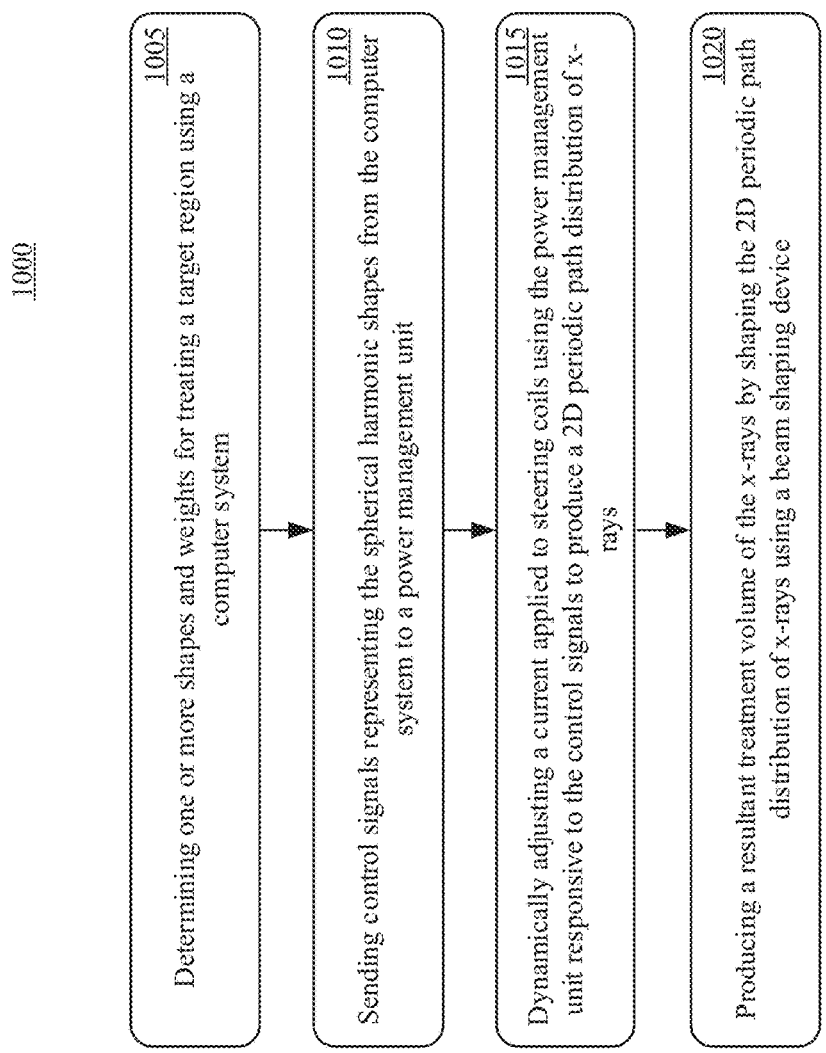
FIG. 10 is a flow chart depicting an exemplary sequence of computer implemented steps for automatically producing a 2D periodic distribution of x-rays from a 2D periodic electron beam path using a radiotherapy system according to embodiments of the present invention.

With regard to FIG. 10, an exemplary sequence of computer implemented steps 1000 for automatically producing a 2D periodic distribution of x-rays using a radiotherapy system is depicted according to embodiments of the present invention. At step 1005, one or more shapes (e.g., spherical harmonic shapes) and corresponding weights for treating a target region are determined using a computer system. The target region may be determined according to a treatment plan generated based on a computed tomography (CT) scan, for example. At step 1010, one or more control signals representing the shapes and weights are transmitted from the computer system to a power management unit. Thereafter, at step 1015, the power management unit dynamically adjusts a current or voltage applied to the steering coils responsive to the control signals to produce x-rays (e.g., a 2D periodic distribution of x-rays) corresponding to the shapes and the weights. At step 1020, a resultant treatment volume of the x-rays is generated by shaping the distribution of x-rays using a beam shaping device. The resultant treatment volume generated by step 1020 can provide higher dosages in a short period of time compared to existing techniques, and can extend the lifetime of the x-ray target by distributing heat across the target surface.

Advantageously, embodiments according to the invention can be implemented without moving parts (e.g., without moving the x-ray target). However, a 2D periodic beam distribution can be achieved by moving the x-ray target with respect to the electron beam. Moving the electron beam with respect to the target reduces target heating and increases beam output.

Figure 11:
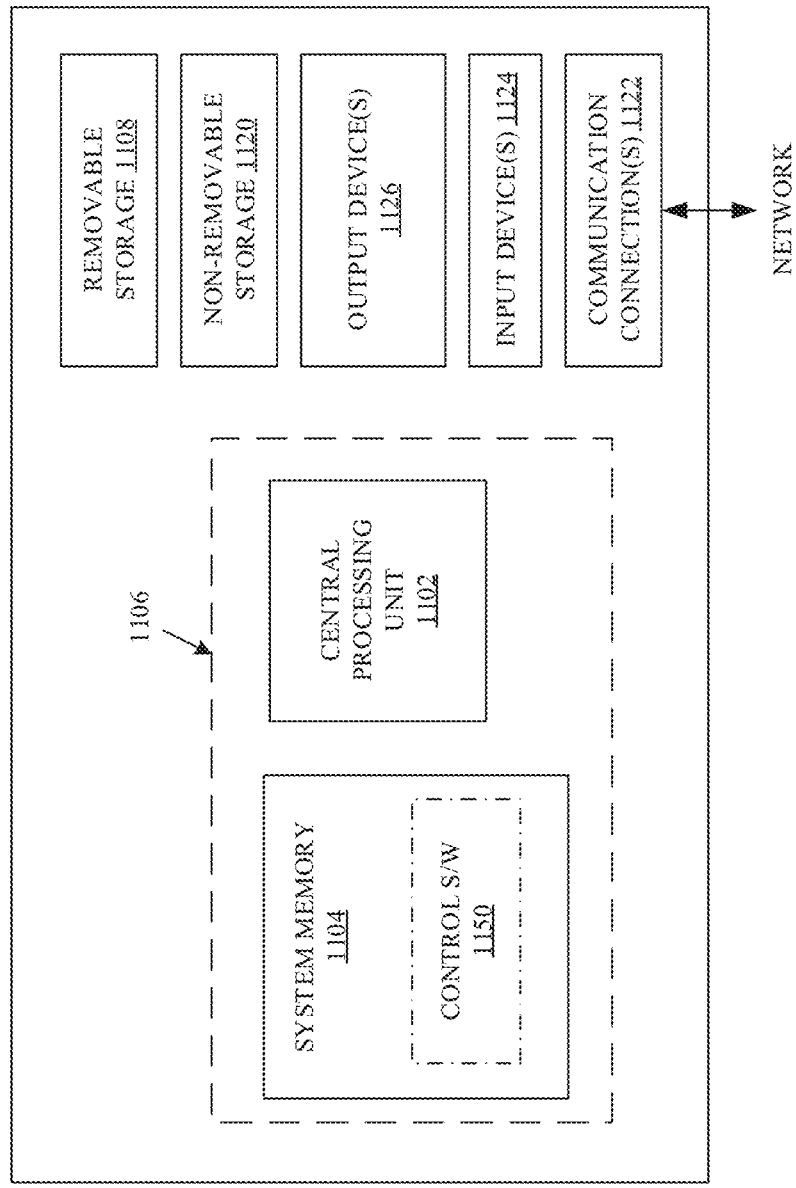
FIG. 11 shows a block diagram of an example of a computing system upon which one or more various embodiments described herein may be implemented in accordance with various embodiments of the present disclosure.

FIG. 11 shows a block diagram of an example of a computing system 1100 upon which one or more various embodiments described herein may be implemented in accordance with various embodiments of the present disclosure. The computer system 1100 may include a cloud-based computer system, a local computer system, or a hybrid computer system that includes both local and remote devices for providing radiotherapy using a 2D periodic distribution of x-rays. In a basic configuration, the system 1100 includes at least one processing unit 1102 and memory 1104. This basic configuration is illustrated in FIG. 11 by dashed line 1106. The system 1100 may also have additional features and/or functionality. For example, the system 1100 may also include additional storage (e.g., removable and/or non-removable) including, but not limited to, magnetic or optical disks or tape. Such additional storage is illustrated in FIG. 11 by removable storage 1108 and non-removable storage 1120.

The system 1100 may also contain communications connection(s) 1122 that allow the device to communicate with other devices, e.g., in a networked environment using logical connections to one or more remote computers. Furthermore, the system 1100 may also include input device(s) 1124 such as, but not limited to, a voice input device, touch input device, keyboard, mouse, pen, touch input display device, etc. In addition, the system 1100 may also include output device(s) 1126 such as, but not limited to, a display device, speakers, printer, etc.

In the example of FIG. 11, the memory 1104 includes computer-readable instructions, data structures, program modules, and the like associated with one or more various embodiments 1150 in accordance with the present disclosure. However, the embodiment(s) 1150 may instead reside in any one of the computer storage media used by the system 1100, or may be distributed over some combination of the computer storage media, or may be distributed over some combination of networked computers, but is not limited to such. The system 1100 may be configured to generate or access a radiotherapy treatment plan and to control one or more steering coils to produce beam paths according to the radiotherapy treatment plan.

It is noted that the computing system 1100 may not include all of the elements illustrated by FIG. 11. Moreover, the computing system 1100 can be implemented to include one or more elements not illustrated by FIG. 11. It is pointed out that the computing system 1100 can be utilized or implemented in any manner similar to that described and/or shown by the present disclosure, but is not limited to such.

Embodiments of the present invention are thus described. While the present invention has been described in particular embodiments, it should be appreciated that the present invention should not be construed as limited by such embodiments, but rather construed according to the following claims.

What is claimed is:

1. A radiotherapy treatment system comprising:
   a computer system;
   an electron emission device for producing and emitting an electron beam;
   a target;
   a plurality of steering coils for providing magnetic fields in perpendicular directions for steering said electron beam to said target, wherein said target generates x-rays responsive to an interaction with said electron beam; and
   a field shaping device configured to be placed between said target and a patient, said field shaping device operable to shape a treatment volume of said x-rays,
   wherein said computer system comprises instructions, that when executed, cause said computer system to control said plurality of steering coils to scan said electron beam across said target in a 2D periodic path to produce a 2D periodic distribution of x-rays.

2. The radiotherapy treatment system as described in claim 1, wherein said electron emission device comprises:
   an electron gun assembly; and
   a linear accelerator coupled to receive electrons from said electron gun assembly, and operable to produce said electron beam emitted from said electron emission device.

3. The radiotherapy treatment system as described in claim 1, wherein said 2D periodic path comprises a Lissajous type shape.

4. The radiotherapy treatment system as described in claim 1, wherein said 2D periodic path comprises spherical harmonic based shapes.

5. The radiotherapy treatment system as described in claim 1, wherein said 2D periodic path comprises a linear combination of an s-wave shape, a p-wave shape, and a d-wave shape.

6. The radiotherapy treatment system as described in claim 5, wherein said 2D periodic path comprises a non-Cartesian shape for shaping the electron beam.

7. The radiotherapy treatment system as described in claim 1, wherein said instructions, when executed, cause said computer system to adjust at least one of a voltage and a current over said plurality of steering coils.

8. A radiotherapy treatment system comprising:
   an electron emission device for producing and emitting an electron beam;
   a target;
   a plurality of steering coils for providing magnetic fields in perpendicular directions for steering said electron beam to said target, wherein said target generates x-rays responsive to an interaction with said electron beam;
   a control device coupled to said plurality of steering coils; and
   a field shaping device comprising a multileaf collimator, said field shaping device configured to be placed between said target and a patient, said field shaping device operable to shape a treatment volume of said x-rays, and wherein said control device is operable to control said plurality of steering coils to cause said electron beam to scan across said target in a 2D periodic path to produce a 2D periodic distribution of x-rays, and wherein further a shape of said 2D periodic path in a combination with a physical configuration and an orientation of said field shaping device define a resultant treatment volume of x-rays exposed to said patient.

9. The radiotherapy treatment system as described in claim 8, wherein said electron emission device comprises:
an electron gun assembly; and
a linear accelerator coupled to receive electrons from said electron gun assembly, and operable to produce said electron beam, wherein said electron beam is of a range from 1 MeV to 300 MeV.

10. The radiotherapy treatment system as described in claim 9, wherein said 2D periodic path comprises a Lissajous type path.

11. The radiotherapy treatment system as described in claim 9, wherein said 2D periodic path comprises spherical harmonic based shapes.

12. The radiotherapy treatment system as described in claim 11, wherein said 2D periodic path comprises a linear combination of an s-wave shape, a p-wave shape, and a d-wave shape.

13. The radiotherapy treatment system as described in claim 8, wherein said control device is operable to control said magnetic fields of said plurality of steering coils by adjusting at least one of a voltage and a current over said plurality of steering coils.

14. A method of generating an x-ray treatment volume using a radiotherapy treatment system, said method comprising:
generating and emitting an electron beam using an electron emission device;
steering said electron beam onto a target and dynamically scanning said electron beam across said target in a 2D periodic path;
producing, via said target, and responsive to an interaction with said electron beam being scanned thereon in accordance with said 2D periodic path, a distribution of x-rays; and
producing a resultant treatment volume of said distribution or x-rays by shaping said distribution of x-rays using a field shaping device, wherein a shape of said 2D periodic path in a combination with a physical configuration and an orientation of said field shaping device define said resultant treatment volume of x-rays.

15. The method as described in claim 14, wherein said electron emission device comprises:
an electron gun assembly; and
a linear accelerator coupled to receive electrons from said electron gun assembly, and operable to produce said electron beam emitted from said electron emission device.

16. The method as described in claim 14, wherein said 2D periodic path comprises a Lissajous type path.

17. The method as described in claim 14, wherein said 2D periodic path comprises spherical harmonic based shapes.

18. The method as described in claim 17, wherein said 2D periodic path comprises a linear combination of an s-wave shape, a p-wave shape, and a d-wave shape.

19. The method as described in claim 14, further comprising adjusting at least one of a voltage and a current over a plurality of steering coils to scan said electron beam across said target in said 2D periodic path.

20. The method as described in claim 14, wherein said 2D periodic path comprises a convex hull.

* * * * *